(12) United States Patent
Holmes, Jr.

(10) Patent No.: US 11,317,904 B2
(45) Date of Patent: *May 3, 2022

(54) KNOTLESS SUTURE ANCHOR WITH INTERNAL SUTURE LOCKING MECHANISM

(71) Applicant: S. Wendell Holmes, Jr., Lexington, SC (US)

(72) Inventor: S. Wendell Holmes, Jr., Lexington, SC (US)

( * ) Notice: Subject to any disclaimer, the term of this patent is extended or adjusted under 35 U.S.C. 154(b) by 226 days.

This patent is subject to a terminal disclaimer.

(21) Appl. No.: 16/723,200

(22) Filed: Dec. 20, 2019

(65) Prior Publication Data
US 2020/0146669 A1 May 14, 2020

Related U.S. Application Data

(63) Continuation of application No. 14/382,234, filed as application No. PCT/US2013/028701 on Mar. 1, 2013, now Pat. No. 10,542,966.

(60) Provisional application No. 61/605,962, filed on Mar. 2, 2012.

(51) Int. Cl.
*A61B 17/04* (2006.01)
*A61B 17/06* (2006.01)

(52) U.S. Cl.
CPC .......... *A61B 17/0401* (2013.01); *A61B 17/04* (2013.01); *A61B 17/06166* (2013.01); *A61B 2017/044* (2013.01); *A61B 2017/0448* (2013.01); *A61B 2017/0451* (2013.01)

(58) Field of Classification Search
CPC ............ A61B 17/0401; A61B 17/0485; A61B 2017/0451; A61B 2017/0446; A61B 2017/0459; A61B 2017/0458; A61B 2017/0403; A61B 2017/0454; A61B 2017/0456; A61B 2017/044

See application file for complete search history.

(56) References Cited

U.S. PATENT DOCUMENTS

| 5,224,946 A | 7/1993 | Hayhurst et al. |
| 2001/0051816 A1 | 12/2001 | Enzerink et al. |

(Continued)

OTHER PUBLICATIONS

International Search Report and Written Opinion of ISA/US, PCT Application Serial No. PCT/US2013/028701, dated May 9, 2013.

*Primary Examiner* — Majid Jamialahmadi
(74) *Attorney, Agent, or Firm* — Fox Rothschild LLP

(57) ABSTRACT

A readily implantable knotless suture anchor that de-couples the angle of insertion of the anchor from the tissue passage step and other steps of conventional procedures. An anchor provides an internal locking mechanism configured such that: suture knots do not have to be tied; suture and tissue tension can be easily adjusted intraoperatively; and suture passage and tensioning can be done at a variety of positions and angles. A method includes: passing a first suture through a patient's tissue and then through a loop of a shuttle suture; pulling the free end of the shuttle suture until the first suture passes through an internal suture locking mechanism; applying tension in the first suture until adequate tension is achieved with respect to the tissue; automatically engaging an internal locking member; and securing the first suture against further relative movement with respect to the anchor.

7 Claims, 4 Drawing Sheets

(56) References Cited

U.S. PATENT DOCUMENTS

| | | | |
|---|---|---|---|
| 2006/0106423 A1* | 5/2006 | Weisel | A61B 17/0487 606/232 |
| 2011/0238113 A1 | 9/2011 | Fanton et al. | |
| 2012/0130423 A1 | 5/2012 | Sengun et al. | |

* cited by examiner

KNOTLESS SUTURE ANCHOR WITH INTERNAL SUTURE LOCKING MECHANISM

This application claims benefit of U.S. Nonprovisional application Ser. No. 14/382,234, filed Aug. 29, 2014; U.S. Provisional Application Ser. No. 61/605,962, filed Mar. 2, 2012; and Patent Cooperation Application No. PCT/US2013/028701 filed Mar. 1, 2013; and the entirety of such applications are incorporated herein by reference.

BACKGROUND

In arthroscopic orthopaedic surgery, it is often necessary to reattach soft tissue to a boney structure. This occurs frequently in the shoulder and other tissues. In these situations where soft tissue is being reattached to bone, it is useful to use a suture anchor device to make the necessary repair. A suture anchor is typically placed into the bone and will not ordinarily pull out. Such suture anchor typically has sutures of its own that can be used to effectively reattach and tie down soft tissue to the bone. This reattachment allows the soft tissue to eventually heal to the bone, and during the process of healing, the suture anchor holds the tissue stationary on the bone.

A suture anchor preferably resists gapping at the tissue bone interface and also resists cyclic loosening of the suture and the tissue from the bone. Anchors can be made of metal, plastic, or absorbable plastics, and designs vary with respect to the number of sutures provided and with respect to whether or not such sutures are allowed to slide within the anchor.

In the normal use of suture anchors, the sutures are passed through the tissue and then knots are tied which allow the anchor to be held into place. A disadvantage can be that suture anchors are normally used for an arthroscopic situation where the anchor is being implanted into a joint where access is limited, and also, where fiber optic arthroscopic cameras are required for visualization by the surgeon. Tying knots in such circumstances can be laborious and time-consuming.

Knotless anchors have been introduced in the surgical device market. However, such anchors may have certain technical pitfalls which the present invention seeks to remedy.

The knotless anchors that have been produced to this point typically involve arthroscopically drilling a hole in a bone, removing the guide from that area, passing sutures through soft tissue. The surgeon must then re-find the hole and insert some sort of push-in anchor or screw-in anchor. As the anchor is screwed or pushed in, it varies as to how much tension is actually developed in the soft tissue. Certain joint geometries and locations make using these types of anchors difficult and/or less effective than desired. The process of drilling the hole and then having to re-find it after removing a specific guide (once the sutures have been passed through the tissue) is a technical difficulty for certain repair locations that have limited access. Additionally, using these types of anchors in certain locations can cause damage to adjacent tissue, which is undesirable.

Accordingly, an anchor design which eliminates the need to tie knots and which provides internal cinching mechanisms would be desirable.

SUMMARY

Generally, the present invention includes, in one embodiment, an easily implantable suture anchor that is knotless, and that de-couples the angle of insertion of the anchor from the tissue passage step and also other steps of the conventional procedure. The present invention anchor provides an internal locking mechanism configured such that: suture knots do not have to be tied; suture and tissue tension can be easily adjusted intraoperatively; and suture passage and tensioning can be done at a variety of positions and angles.

In one exemplary use of the present invention, a surgeon would pass a first suture through the patient's tissue and then through a loop of a shuttle suture. The free end of a shuttle suture would then be pulled until the first suture passes through an internal suture locking mechanism constructed in accordance with the present invention. Tension would be applied in the first suture until adequate tension is achieved with respect to the tissue, and then the internal locking member automatically engages and secures the first suture against further relative movement with respect to the anchor.

In another embodiment of an internal locking mechanism constructed in accordance with the present invention, the desired tension is applied in the first suture with respect to the tissue, and then the other end of a line or suture, i.e., a "locking limb," is pulled in the opposite direction until the internal locking mechanism locks the first suture in place.

In either case, excess suture extending outwardly from the tissue is then cut and removed.

In another exemplary implementation of the present invention, an anchor for implantation in tissue and for use in cooperation with a suture is provided and includes a body member and a cleat connected to the body member that moves between a locking position and an unlocking position. The cleat engages the suture upon being in the locking position and generally fixes movement of the suture with respect to the body member. The cleat substantially permits relative movement between the suture and the body member upon being in the unlocking position, and the cleat automatically moves from the unlocking position to the locking position upon the suture being drawn in a predetermined direction, wherein the anchor is secured to the tissue.

In another implementation, the apparatus further comprises a plurality of teeth being provided on the cleat for engaging the suture upon the cleat being in the locking position.

A further exemplary implementation includes an anchor for implantation in tissue and for use in cooperation with a suture, comprising a body member and a snap lock mechanism connected to the body member that moves between a locking position and an unlocking position. The snap lock mechanism engages the suture upon being in the locking position and generally fixes movement of the suture with respect to the body member. Additionally, the snap lock mechanism substantially permits relative movement between the suture and the body member upon being in the unlocking position, and a line is connected to the snap lock mechanism that moves the snap lock mechanism from the unlocking position to the locking position upon the line being drawn in a predetermined direction, wherein the anchor is secured to the tissue.

In another implementation of the present invention the snap lock device is conically shaped.

The present invention also includes in an exemplary implementation a method for implantation of a suture anchor in tissue, comprising: providing a first suture; providing a shuttle suture; providing an internal suture locking mechanism having a suture lock; passing the first suture through the tissue and then through a loop of the shuttle suture; pulling the free end of a shuttle suture until the first suture passes through the internal suture locking mechanism;

applying tension in the first suture until desired tension is achieved with respect to the tissue; and allowing the suture lock to automatically engage and secure the first suture against relative movement with respect to the anchor.

Further, a method of the present invention may further comprise applying tension in the first suture with respect to the tissue from one end of the first suture, and through use of the other end of the first suture, pulling in the opposite direction until the suture lock locks the first suture against relative movement with respect to the anchor.

BRIEF DESCRIPTION OF THE DRAWINGS

The drawings referenced herein form a part of the specification. Features shown in the drawings are meant as illustrative of some, but not all, embodiments of the invention, unless otherwise explicitly indicated, and implications to the contrary are otherwise not to be made. Although in the drawings like reference numerals correspond to similar, though not necessarily identical, components and/or features, for the sake of brevity, reference numerals or features having a previously described function may not necessarily be described in connection with other drawings in which such components and/or features appear.

DESCRIPTION OF PREFERRED EMBODIMENTS

Figure 1:
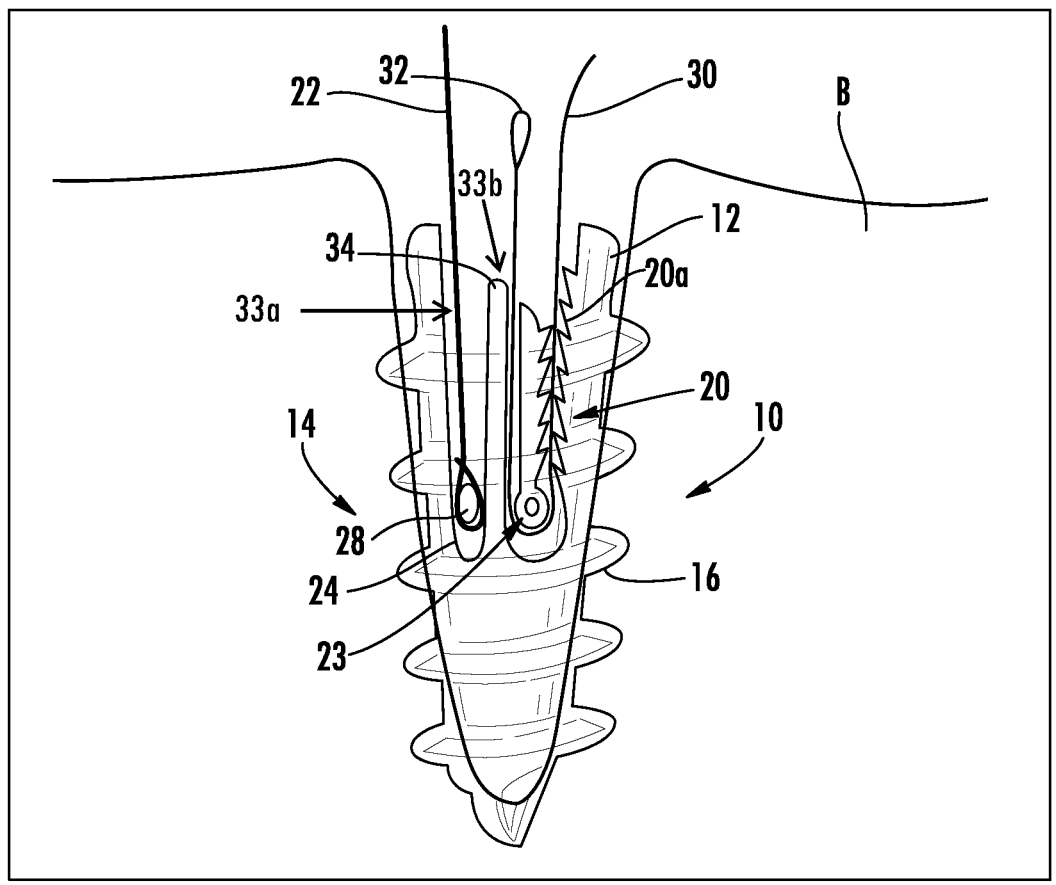
FIG. 1 is a perspective view, with parts cut away, of a knotless suture anchor with an internal suture locking mechanism constructed in accordance with the present invention.

The accompanying drawings and the description which follows set forth this invention in several of its preferred embodiments. However, it is contemplated that persons generally familiar with surgical devices will be able to apply the novel characteristics of the structures illustrated and described herein in other contexts by modification of certain details. Accordingly, the drawings and description are not to be taken as restrictive on the scope of this invention, but are to be understood as broad and general teachings.

Referring now to the drawings in detail, wherein like reference characters represent like elements or features throughout the various views, the knotless suture anchor (also referred to herein as "suture anchor" and as simply "anchor") with an internal suture locking mechanism of the present invention is indicated generally in the figures by reference character 10.

Figure 2:
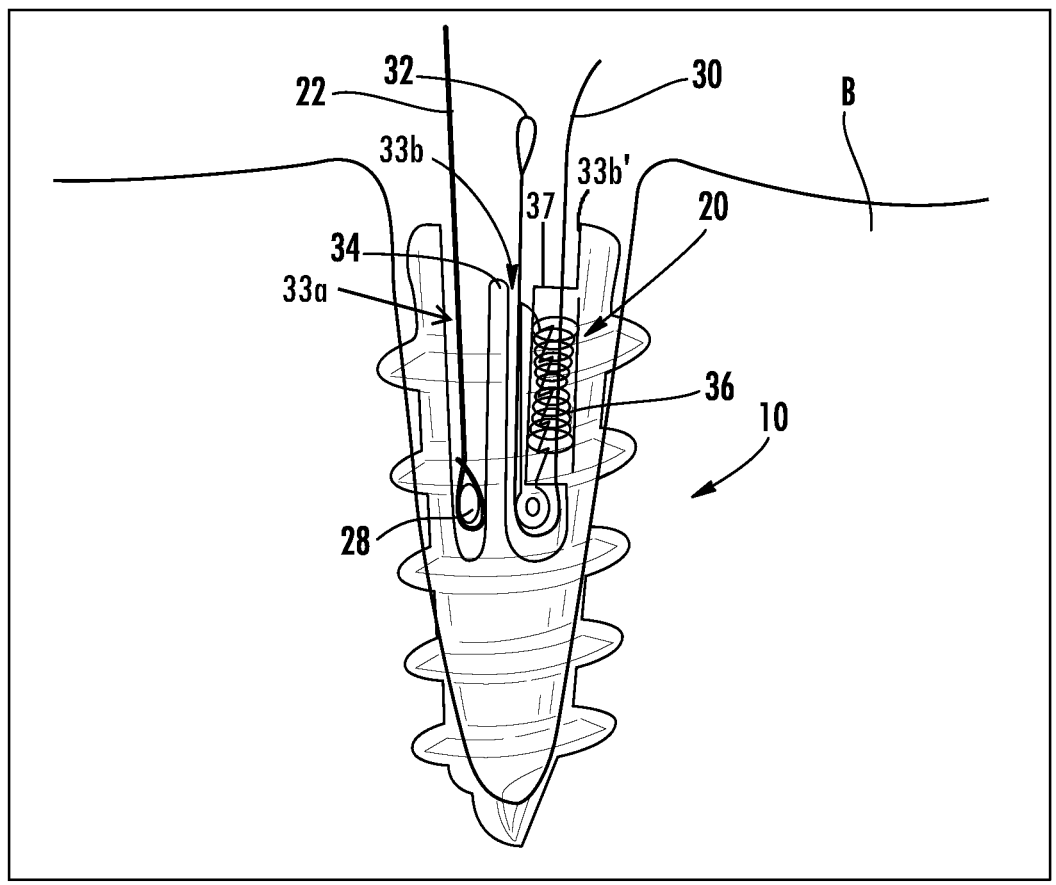
FIG. 2 is a perspective view, with parts cut away, of an alternate embodiment of a knotless suture anchor with an internal suture locking mechanism constructed in accordance with the present invention.
Figure 3:
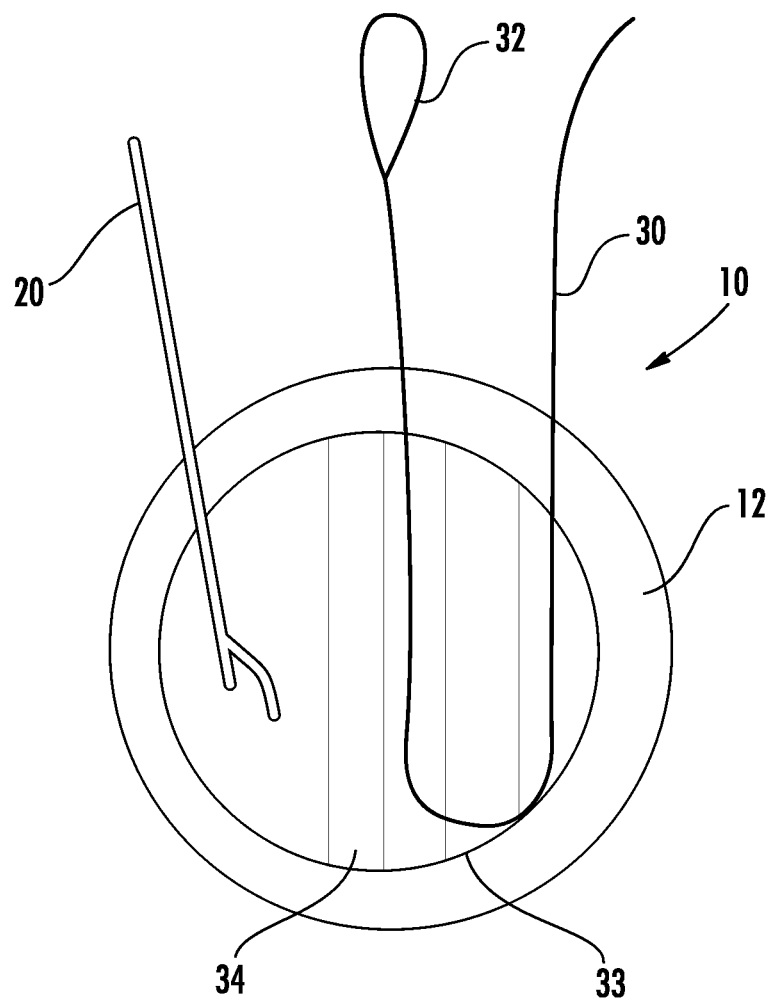
FIG. 3 is a plan view of a knotless suture anchor with an internal suture locking mechanism constructed in accordance with the present invention.

As shown in FIGS. 1-3, suture anchor 10 includes a shell, generally 12, which may be similar to conventional suture anchors. Shell 12 may include, in one preferred embodiment, a screw-in portion 14 having threaded portions 16 and/or a tap-in configuration (not shown) with either barbs or threads, based on whether anchor 10 is to be tapped in or screwed into the bone, generally B.

Body member, or shell, 12 may be constructed of a non-absorbable plastic polymer, bioabsorbable plastic polymer, metal, or some other suitable and implantable material. An internal mechanism, generally 20, of anchor 10 may include one or more high-strength braided nylon sutures, generally 22, with one end of such suture 22 being fixed, as shown in FIGS. 1 and 2, in an elongated passage 33a, which extends generally parallel to an elongated passage 33b, both passages 33a, 33b being defined by a guide 34 in the body, generally 24, of anchor 10. Such fixation of suture 22 to body 24 can be done in various ways. One way includes actually fusing suture 22 to a polymer portion of body 24. Other ways may include using some sort of post, such as post 28, about which suture 22 can be securely looped around and tied within anchor 10.

As shown in FIGS. 1-3, in addition to suture 22, anchor 10 may also include, in one preferred embodiment, a heavy monofilament nylon shuttle suture, generally 30, placed in anchor 10. Shuttle suture 30 has two free ends, one having a suture loop 32 which provides a shuttle through anchor 10, once the loop 32 has been passed through tissue (not shown). Once loop 32 is passed through anchor 10 via passage 33b defined by guide 34, internal locking mechanism 20 then allows both the suture shuttle and the braided nylon suture 22 (which passes through loop 32 of shuttle suture 30) to be pulled through anchor 10 in a uni-directional fashion, with internal locking mechanism 20 cinching suture 22 by acting as an internal locking cleat 23, wherein suture 22 can pass one way but not the other. Accordingly, as the free end of shuttle suture 30 is gradually pulled, it initially passes through internal locking mechanism 20, but eventually, with continued pulling of shuttle suture 30, suture 22 passes into passage 33b and through internal locking mechanism 20 to ultimately cinch the tissue down (the tension may be adjusted in the tissue tension "rolling" tissue in either direction), such that the tissue is pulled down to the hone Bin and/or near the suture anchor 10. This allows re-approximation of the attachment of the tissue to the bone and allows adjustment of the tension both within suture 22, and thus also the tissue to attach itself to bone B.

Internal locking mechanism 20 can be of various configurations, and the present invention is not to be limited to the mechanisms disclosed and/or shown herein. Multiple other internal locking mechanisms could be used in anchor 10, and the internal locking mechanisms disclosed and/or shown herein are for illustrative purposes and are not intended to limit the scope of the internal mechanisms that could be used in connection with anchor 10.

One variation of internal locking mechanism 20 is shown in FIG. 1 and could be a series of opposing resilient, directional barbs, or teeth, 20a which allow suture 22 to be pulled in between teeth 20a in only one, i.e., a "first" direction. An attempt to pull suture 22 in the other ("second") direction would cause the teeth 20a to engage and hold suture 22 against further movement in the second direction. However, in the event suture 22 is again pulled in the first direction, teeth 20a would release suture 22 to allow suture 22 to again be pulled in the first direction. Internal locking mechanism 20 thus allows passage of sutures 30, 22 in one direction, but not in the opposite direction.

Another variation of internal locking mechanism 20 could be an internal pre-tied locking knot, such as a hangman's noose knot 36 adjacent a projection 37 along a sidewall 33b' of passage 33b, as shown in FIG. 2, As also shown in FIG. 2, shuttle suture 30 passes downwardly in passage 33b in a first direction and then reverses direction before passing upwardly into and through knot 36. Similarly, as shown in FIG. 1, shuttle suture 30 passes downwardly in passage 33*b* in a first direction and then reverses direction before passing upwardly into and through teeth 20*a* of internal locking mechanism 20.

Still another variation (not shown) could be a woven suture inside a suture anchor which once again allows uni-directional passage of the braided nylon suture. This could be a configuration similar to a Chinese finger trap type of device, which tightens against the suture moving in a predetermined direction.

Figure 4:
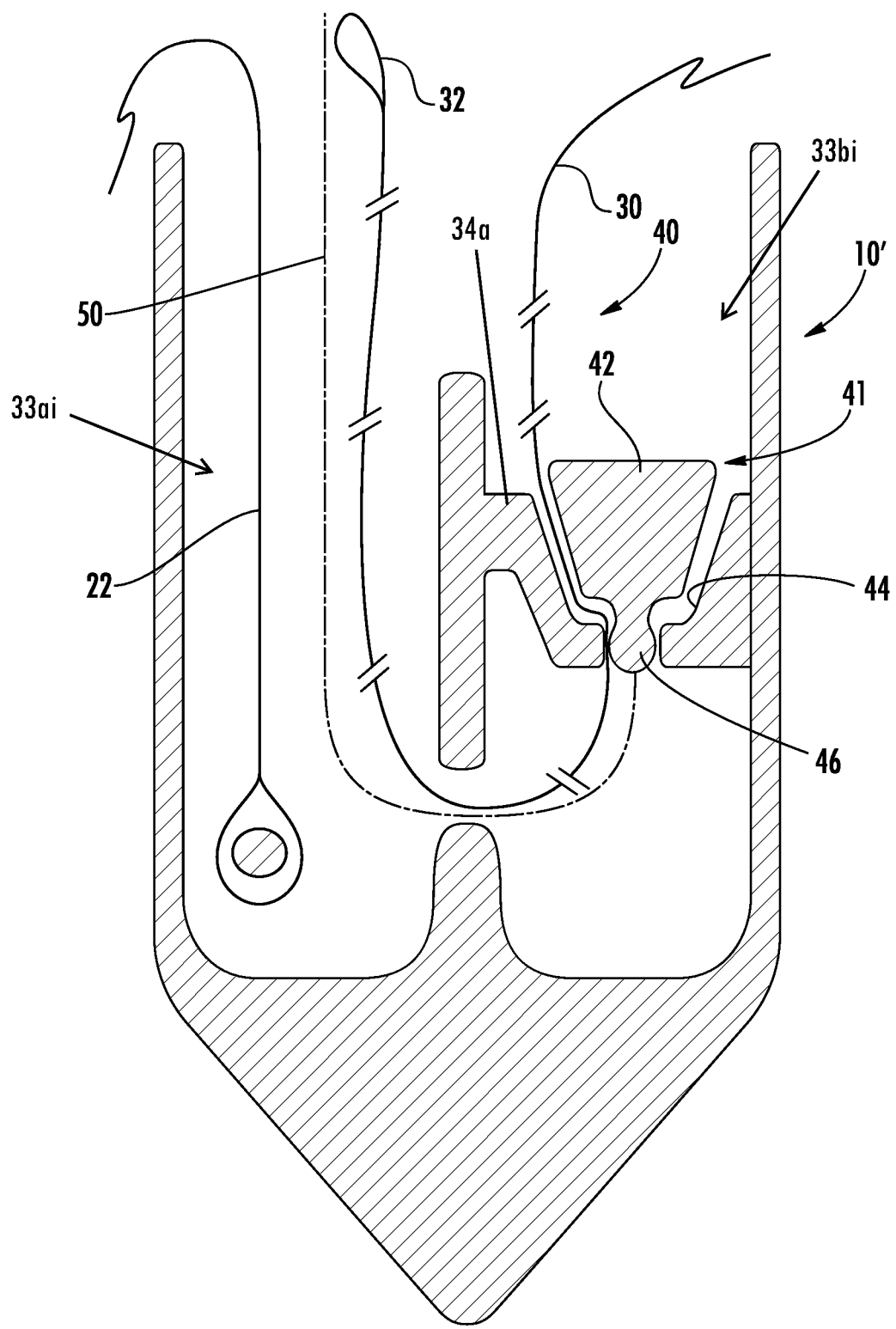
FIG. 4 is a sectional view of an alternate embodiment of a knotless suture anchor with an internal suture locking mechanism constructed in accordance with the present invention.

Other variations could include, but are not limited to, a conical locking mechanism, generally 40, as shown in anchor 10' in FIG. 4. Conical snap locking mechanism, generally 41, includes a generally conical member 42 which is biased by weight and/or spring force towards a seat 44. Although not shown, a strap, cable, line, or the like could be used to prevent member 42 from falling out of anchor 10'. One end of suture 22 is fixed, as shown in FIG. 4, in an elongated passage 33*ai*, which extends generally parallel to an elongated passage 33*bi*, both passages 33*ai*, 33*bi* being defined by a guide 34*a* in the body of anchor 10'. Suture 22 may pass in a first downward direction in passage 33*ai* and then reverse direction and pass upwardly through an opening in seat 44, whereby member 42 is caused to be lifted slightly above seat 44, to thereby form a passage for suture 22. As also shown in FIG. 4, loop 32 (which carries suture 22 therewith) of shuttle suture 30 passes downwardly in passage 33*ai* in a first downward direction and then reverses direction before passing upwardly into and through passage 33*bi* and the opening in seat 44.

If suture 22 is pulled in the other ("second") direction, however, member 42 automatically moves downwardly, with neck portion 46 ultimately seating in a snap-fit, interference-fit arrangement with respect to seat 44 and engages suture 22 and fixes it against movement in the second direction. Similarly, as discussed above with respect to other versions of internal locking mechanism 20, in use, the surgeon would pass suture 22 through the patient's tissue and then load suture 22 in and through loop 32. The free end of shuttle suture 30 would then be pulled until suture 22 (moving in the first direction) passes through anchor 10. Tension would be applied in suture 22 until adequate tension is achieved, and then the other free end of a second, line or suture, 50, the "locking limb," which has its other end connected to member 42, is pulled in the second direction until the conical snap locking mechanism 41 locks suture 22 in place. Excess suture extending outwardly from the tissue is then cut and removed.

Further, a cam mechanism (not shown) could be provides that flips back to lock upon itself in the event suture is pulled in reverse fashion.

It is to be understood that the above various internal locking mechanism configurations could be used either singularly or in combination with one another in a given anchor 10, if desired.

Conventional knotless anchor designs generally marry the angle of insertion of the anchor to a portal, since the anchor has to be placed through the portal, and then suture passage through tissue must be achieved. At this point, the anchor position must be re-found through the same portal. Then, the tissue is cinched down. However, for certain positions, in the shoulder in particular, this creates a technical problem, because frequently it is in an inappropriate location to place a portal. For example, in repairing a superior labrum or SLAP lesion, anchors are frequently placed percutaneously through the rotator cuff. It is advantageous in this situation to make these perforations through the rotator cuff as small as possible. However, normally a 6-8 mm diameter cannula is required to be inserted through this tissue in order to position conventional cinching knotless suture anchor designs.

With anchor 10 of the present invention, anchor 10 could be placed percutaneously through a 3 or 4 mm hole, and then the surgeon would have the freedom to pass the suture through tissue in a variety of other angles within the shoulder. This would likely minimize damage to the adjacent tissue, particularly with respect to the rotator cuff noted in the example above. Labral repair is but one application of the present invention. Anchor 10 could also be used in other repairs, such as rotator cuff repair in the shoulder, biceps tenodesis, and a myriad of other procedures in the shoulder and elsewhere. Anchor 10 could be used in any other joint in the body in which suture anchor placement is required for soft tissue fixation to bone.

In short, anchor 10 provides a versatile device which could be used in the shoulder, in particular, and for numerous other applications in the musculoskeletal system to facilitate soft tissue fixation to bone, with minimal suture damage. The present invention may find particular applications in procedures involving the: shoulder (labrum, rotator cuff, biceps tenodesis, etc.); knee (backup hamstring fixation, MCL/LCL reconstruction, ligament avulsions, etc.); elbow (UCL/LUCL reconstruction, biceps, etc.); foot and ankle; and wrist. The present invention also provides a lower profile by eliminating prominent knots on articulating surfaces.

Aspects of the present invention may include a braided nylon suture with one end fixed to an anchor, a heavy monofilament nylon suture shuttle, internal locking mechanisms with multiple variations, and a simplified methodology of how a knotless suture anchor with an internal suture locking mechanism may be constructed in accordance with the present invention might be inserted and used. Also disclosed is a simplified technique for insertion and use of an anchor of the present invention. For example, in methods disclosed herein, suture 22 can be single or double loaded as applicable.

Anchors 10, 10' can be produced in various diameters, including without limitation, diameters between approximately 2 and 6 millimeters.

The present invention thus provides, among other things, the potential of decreased surgical time, increased surgical accuracy, a decreased dependence on knot-tying and loosening, lower profile by eliminating prominent knots on articulating surfaces.

Specifically, the knotless anchor of the present invention may be inserted through drilling cannula (which reduces the likelihood of losing the hole), and a "normal" suture passage may be used. Also, tissue tension may be adjusted by "rolling" tissue in either direction. This can thus address problems which may occur with current anchor designs, such as losing the hole in the methodology where a hole is drilled, and the devise is removed. Then, the hole must be relocated. This can pose particular difficulty in relation to the lower glenoid quadrants. Additionally, the angle of insertion of such a conventional anchor may be married to a working portal. Moreover, with such designs, it may be difficult to manipulate tissue as a suture is tensioned.

In one exemplary implementation, anchor 10 may include a standard tap-in or screw-in insertion that permits drilling and insertion through the same cannula, which may be 3.0 to 4.5 mm cannula, and as noted above, the anchor may be single or double loaded. Anchor 10 may include suture 22 being a wire fixed on one end in the anchor and with a free end. A heavy nylon suture shuttle may be preloaded, and an internal locking mechanism may include a cleat, a locking knot, and a Chinese finger trap type device. Other variations of the present invention could include a Chinese finger trap type device including a suture-in suture with unidirectional tensioning, an internal cam, and a second suture to lock a know when adequate tension has been obtained.

While preferred embodiments of the invention have been described using specific terms, such description is for present illustrative purposes only, and it is to be understood that changes and variations to such embodiments, including but not limited to the substitution of equivalent features or parts, and the reversal of various features thereof, may be practiced by those of ordinary skill in the art without departing from the spirit or scope of the present disclosure.

What is claimed is:

1. An anchor for implantation in tissue, the anchor comprising:
    a shell having a guide and a first passage and a second passage defined by the guide;
    a first suture fixedly attached in the first passage of the shell;
    an internal locking mechanism proximate to the second passage of the shell having a movable cleat, wherein the internal locking mechanism is closer to the second passage than the first passage;
    a shuttle suture having two ends, one of the two ends having a suture loop configured to receive the first suture and the other of the two ends having a free end; and
    the shuttle suture passing downwardly in the second passage and looping upwardly into and through the internal locking mechanism,
    wherein, upon the first suture being received by the suture loop and the free end of the shuttle suture being pulled, the first suture first passes into the second passage of the shell and then into the internal locking mechanism, and the internal locking mechanism locks the first suture to the anchor.

2. The anchor of claim 1, further comprising:
    a post in the first passage; and
    the first suture being attached to the post.

3. The anchor of claim 1, further comprising:
    the shell defining a sidewall adjacent the second passage and teeth defined along the sidewall configured for engaging the first suture; and
    wherein the movable cleat includes teeth configured for engaging the first suture.

4. A method for implantation of a suture in tissue, comprising:
    providing a suture anchor including a shell having a first passage, a second passage defined by a guide, a first suture fixedly attached in the first passage, and an internal locking mechanism proximate to the second passage having a movable cleat, wherein the internal locking mechanism is closer to the second passage than the first passage;
    providing a shuttle suture having two ends, one of the two ends having a suture loop configured to receive the first suture and the other of the two ends having a free end, the shuttle suture passing downwardly in the second passage of the shell and looping upwardly into and through the internal locking mechanism;
    passing the first suture through the tissue and then through the suture loop;
    pulling the free end of the shuttle suture until the first suture first passes into the second passage of the shell and then into the internal locking mechanism;
    applying tension in the first suture until desired tension is achieved with respect to the tissue,
    wherein the internal locking mechanism locks the first suture to the shell.

5. The method of claim 4, wherein the pulling until the entirely of the shuttle suture travels through the internal locking mechanism.

6. An anchor for implantation in tissue using a first suture, the anchor comprising:
    a shell having a guide and a first passage and a second passage defined by the guide;
    a member in the first passage of the shell configured for fixed attachment of the first suture;
    an internal locking mechanism proximate to the second passage of the shell having a movable cleat, wherein the internal locking mechanism is closer to the second passage than the first passage;
    a shuttle suture having two ends, one of the two ends having a suture loop configured to receive the first suture and the other of the two ends having a free end; and
    the shuttle suture passing downwardly in the second passage and looping upwardly into and through the internal locking mechanism,
    wherein, upon the first suture being received by the suture loop and the free end of the shuttle suture being pulled, the first suture first passes into the second passage of the shell and then into the internal locking mechanism, and the internal locking mechanism locks the first suture to the anchor.

7. An anchor for implantation in tissue using a first suture, the anchor comprising:
    a shell having a guide and a first passage and a second passage defined by the guide;
    a member in the first passage of the shell configured for fixed attachment of the first suture;
    an internal locking mechanism proximate to the second passage of the shell, wherein the internal locking mechanism is closer to the second passage than the first passage;
    a shuttle suture having two ends, one of the two ends having a suture loop configured to receive the first suture and the other of the two ends having a free end; and
    the shuttle suture passing downwardly and looping upwardly into and through the internal locking mechanism,
    wherein, upon the first suture being received by the suture loop and the free end of the shuttle suture being pulled, the first suture first passes into the second passage of the shell and then into the internal locking mechanism, and the internal locking mechanism locks the first suture to the anchor.

* * * * *